US00PP34950P2

(12) United States Plant Patent
Nelson et al.

(10) Patent No.: US PP34,950 P2
(45) Date of Patent: Jan. 31, 2023

(54) STRAWBERRY PLANT NAMED 'BG-11.3209'

(50) Latin Name: *Fragaria ananassa*
Varietal Denomination: BG-11.3209

(71) Applicant: BERRY GENETICS, INC., Freedom, CA (US)

(72) Inventors: Steven D. Nelson, Watsonville, CA (US); Michael D. Nelson, Watsonville, CA (US); Leo W. Stoeckle, Moorpark, CA (US)

(73) Assignee: Berry Genetics, Inc., Freedom, CA (US)

( * ) Notice: Subject to any disclaimer, the term of this patent is extended or adjusted under 35 U.S.C. 154(b) by 0 days.

(21) Appl. No.: 17/877,003

(22) Filed: Jul. 29, 2022

(51) Int. Cl.
*A01H 5/08* (2018.01)
*A01H 6/74* (2018.01)

(52) U.S. Cl.
USPC ..... Plt./208

(58) Field of Classification Search
USPC ..... Plt./156, 208, 209
See application file for complete search history.

(56) References Cited

U.S. PATENT DOCUMENTS

| | | | |
|---|---|---|---|
| PP17,725 | P3 | 5/2007 | Nelson et al. |
| PP27,441 | P3 | 12/2016 | Nelson et al. |
| PP29,794 | P2 | 11/2018 | Nelson et al. |

*Primary Examiner* — Karen M Redden
(74) *Attorney, Agent, or Firm* — Foley & Lardner LLP

(57) ABSTRACT

This invention relates to a new and distinct variety of strawberry plant named 'BG-11.3209'. This new strawberry plant named 'BG-11.3209' is primarily adapted to the growing conditions of the central coast of California, and is primarily characterized by its red fruit color, large fruit size, and conical fruit shape; very good fruit flavor, with seeds typically held level with to above the surface; firm fruit, with calyx typically raised and sepal attitude generally outward to upward; medium plant size, upright in habit, with medium density and vigor; medium yellow green foliage color, and medium foliage size; and fruiting trusses typically visible above the foliage, with medium to weak pubescence and medium to strong anthocyanins.

5 Drawing Sheets

Latin name of the genus and species of the plant claimed: *Fragaria ananassa.*
Variety denomination: 'BG-11.3209'.

BACKGROUND OF THE INVENTION

The present invention relates to a new and distinct strawberry variety named 'BG-11.3209'. This new variety is a result of a controlled cross made in 2011 in an ongoing breeding program between strawberry variety designated 'BG-99.1975' (U.S. Plant Pat. No. 17,725) as the seed (female) parent, and strawberry variety designated 'BG-4.370' (U.S. Plant Pat. No. 27,441) as the pollen (male) parent. The variety is botanically known as *Fragaria ananassa.*

The seedling resulting from the aforementioned cross was selected from a controlled breeding plot in Ventura County, Calif. in the spring of 2013. After its selection, the new variety was asexually propagated by stolons in both Siskiyou County, Calif. and San Joaquin County, Calif. The new variety was extensively tested over the next several years in fruiting fields in Ventura County, Calif. This propagation has demonstrated that the combination of traits disclosed herein as characterizing the new variety are fixed and remain true-to-type through successive generations of asexual reproduction.

BRIEF SUMMARY OF THE INVENTION

'BG-11.3209' is primarily adapted to the climate and growing conditions of the central coast of California. The nearby Pacific Ocean provides the humidity and moderate temperatures needed to produce a strong, vigorous plant and maintain fruit quality during the winter and spring production months.

The following traits have been repeatedly observed and are determined to be unique characteristics of 'BG-11.3209', which in combination distinguish this strawberry plant as a new and distinct variety:

1. Fruit is red in color, large in size, and conical in shape;
2. Fruit has very good flavor, with seeds typically held level with to above the surface;
3. Fruit is firm, with calyx typically raised and sepal attitude generally outward to upward;
4. Plant is medium in size, upright in habit, with medium density and vigor;
5. Foliage is medium yellow green in color, and medium in size; and
6. Fruiting trusses are typically visible above the foliage, with medium to weak pubescence and medium to strong anthocyanins.

The strawberry variety that is believed to be most closely related to the new variety 'BG-11.3209' is 'BG-9.3142' (U.S. Plant Pat. No. 29,794). In side-by-side comparisons to the similar strawberry variety 'BG-9.3142', 'BG-11.3209' differs by the following combination of characteristics as described in Table 1.

TABLE 1

| Characteristic | 'BG-11.3209' | 'BG-99.3142' (U.S. Plant Pat. No. 29,794) |
|---|---|---|
| Fruit: color | Red | Orange red |
| Fruit: size | Large | Medium |
| Fruit: difference in shape between primary and secondary fruit | Slight to moderate | None or very slight |
| Fruit: flavor | Very good | Excellent |
| Fruit: position of calyx attachment | Ranges from level to raised | Inserted |
| Fruit: keeping quality | Ranges from good to moderate | Excellent |
| Terminal leaf: length/width ratio | As long as broad | Longer than broad |
| Terminal leaf: shape of base | Obtuse | Acute |
| Foliage: shape in cross section | Strongly to slightly concave | Flat to slightly convex |

For identification, a series of molecular markers have been determined for this new variety.

'BG-11.3209' differs from its parents, 'BG-99.1975' and 'BG-4.370' by the following combination of characteristics as described in Tables 2 and 3.

TABLE 2

| Characteristic | 'BG-11.3209' | 'BG-99.1975' (U.S. Plant Pat. No. 17,725) |
|---|---|---|
| Fruit: color | Red | Orange red |
| Fruit: size | Large | Medium |
| Fruit: insertion of achenes | Ranges from level with to above the surface | Below the surface |
| Fruit: position of calyx attachment | Ranges from level to raised | Inserted |
| Plant: size | Medium | Large |

TABLE 3

| Characteristic | 'BG-11.3209' | 'BG-4.370' (U.S. Plant Pat. No. 27,441) |
|---|---|---|
| Fruit: color | Red | Orange red |
| Fruit: position of calyx attachment | Ranges from level to raised | Inserted |
| Fruit: firmness | Firm | Medium |
| Fruit: flavor | Very good | Fair |
| Plant: density | Medium | Ranges from medium to sparse |

BRIEF DESCRIPTIONS OF THE PHOTOGRAPHS

The accompanying color photographs illustrate the overall appearance of typical specimens of the new strawberry variety 'BG-11.3209' at various stages of development, as true as it is reasonably possible with color reproductions of this type. Color in the photographs may differ slightly from the color value cited in the botanical descriptions which accurately describe the color of 'BG-11.3209'. The depicted plant and plant parts of the new strawberry variety 'BG-11.3209' are approximately five to six months old. The photographs were taken in Ventura County, Calif.

DETAILED BOTANICAL DESCRIPTION

Figure 1:
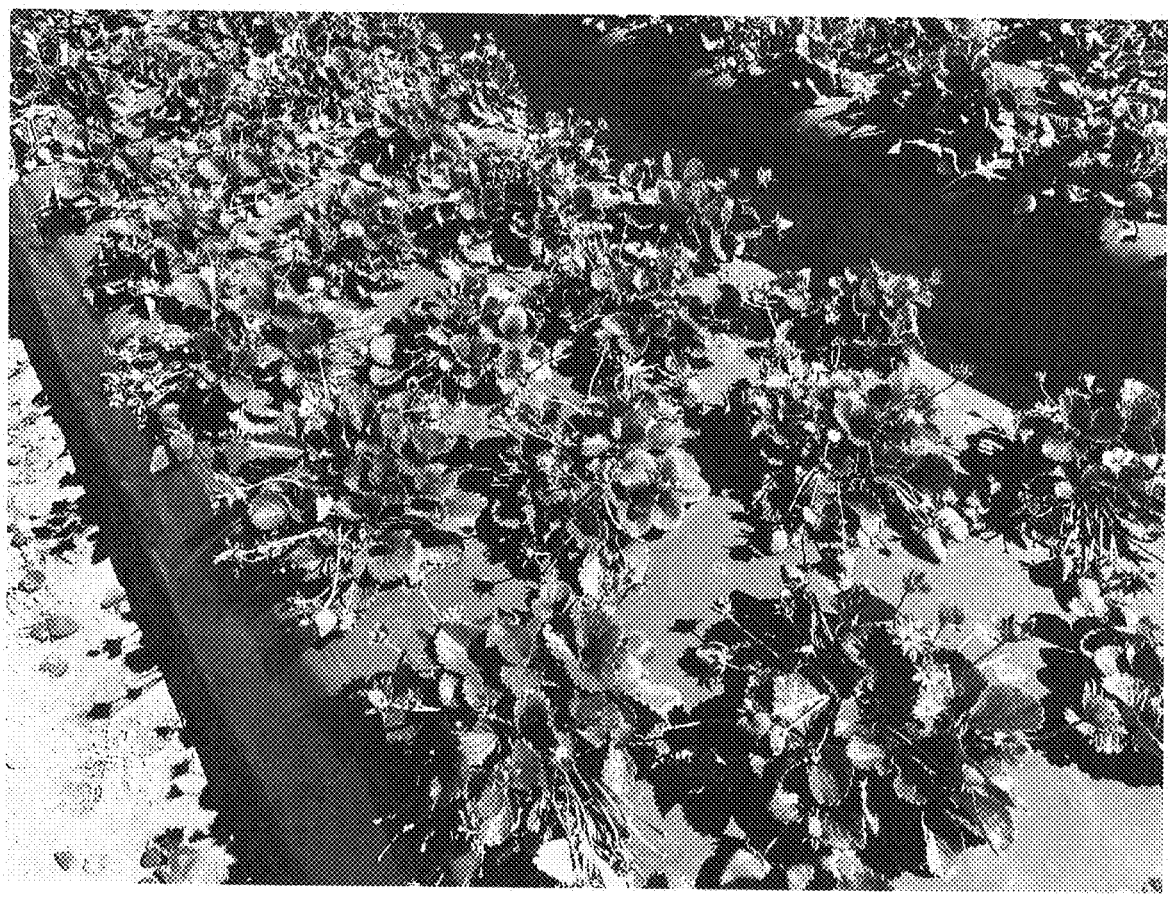
FIG. 1 shows fruiting field characteristics of 'BG-11.3209', taken in the month of March 2022.
Figure 2:
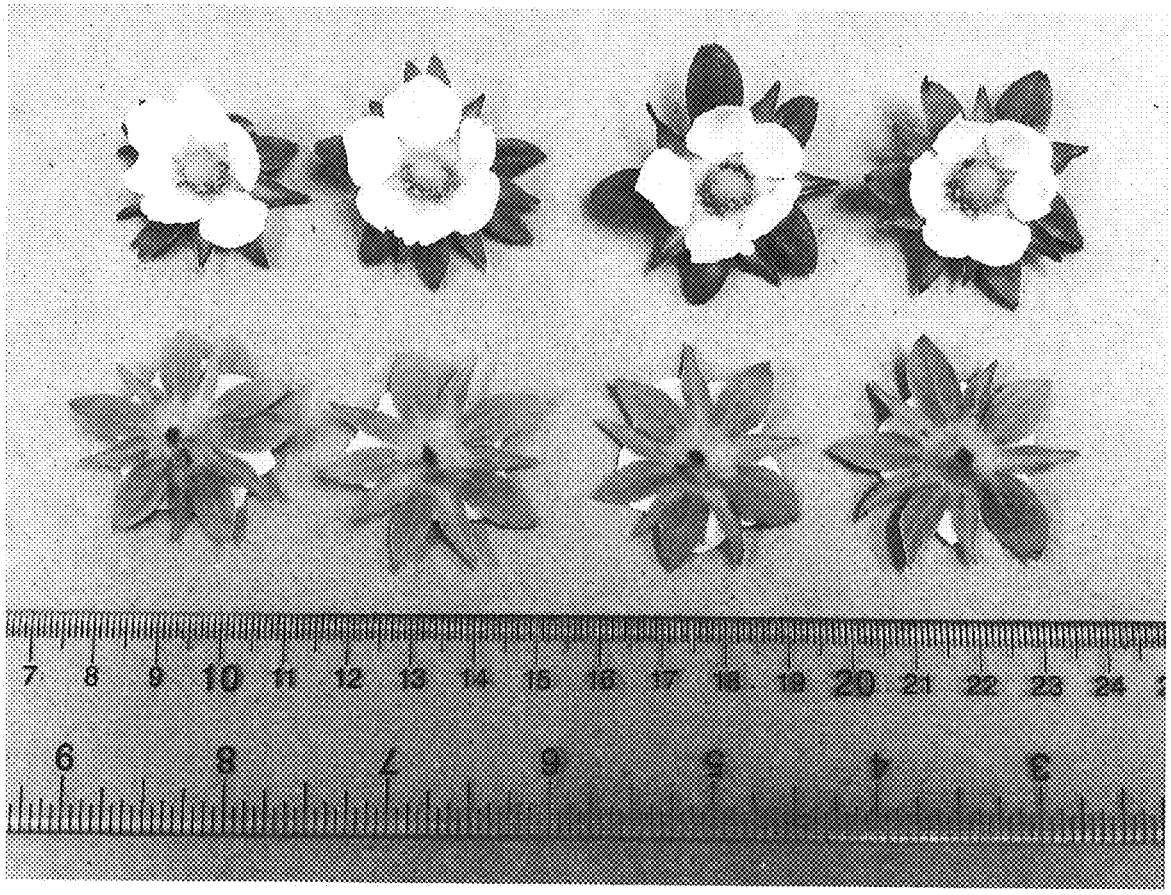
FIG. 2 shows upper and lower surfaces of flower and flower parts of 'BG-11.3209', taken in the month of April 2022.
Figure 3:
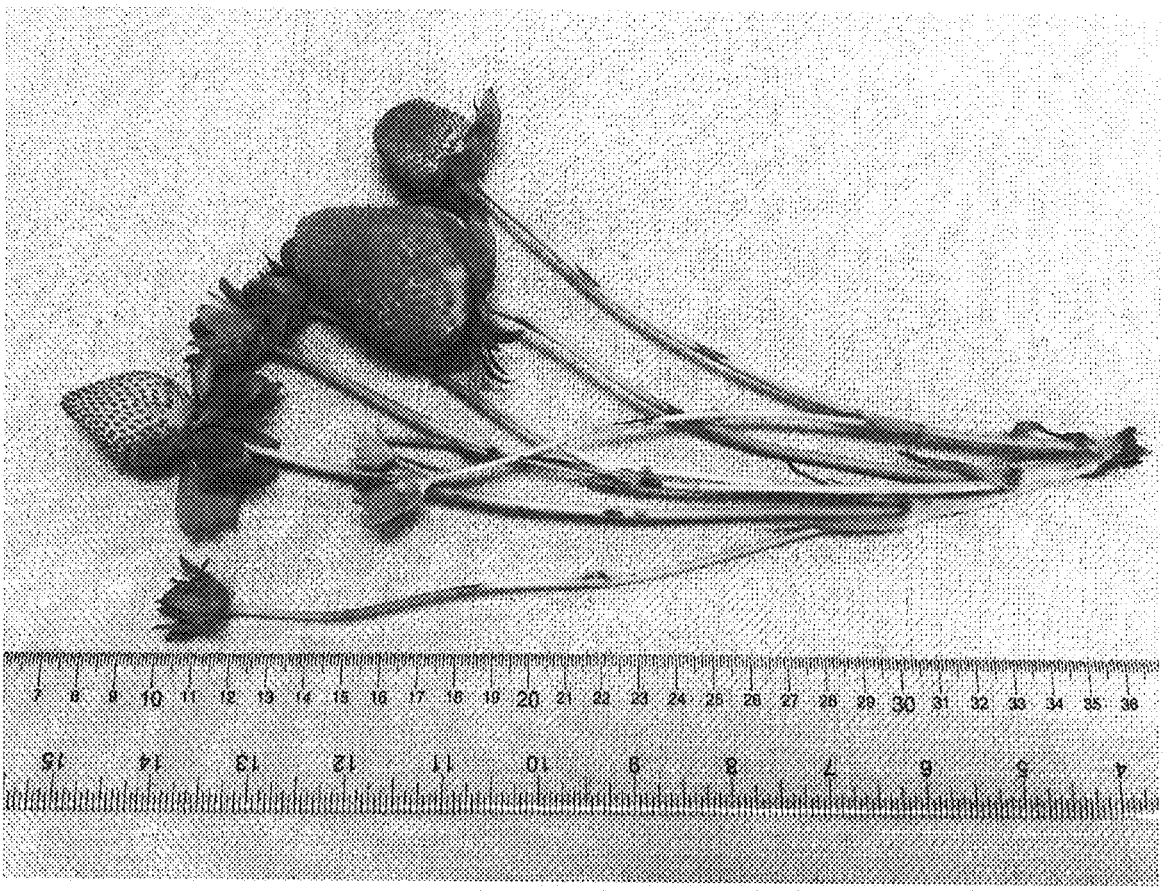
FIG. 3 shows typical fruiting truss and truss parts of 'BG-11.3209', taken in the month of April 2022.
Figure 4:
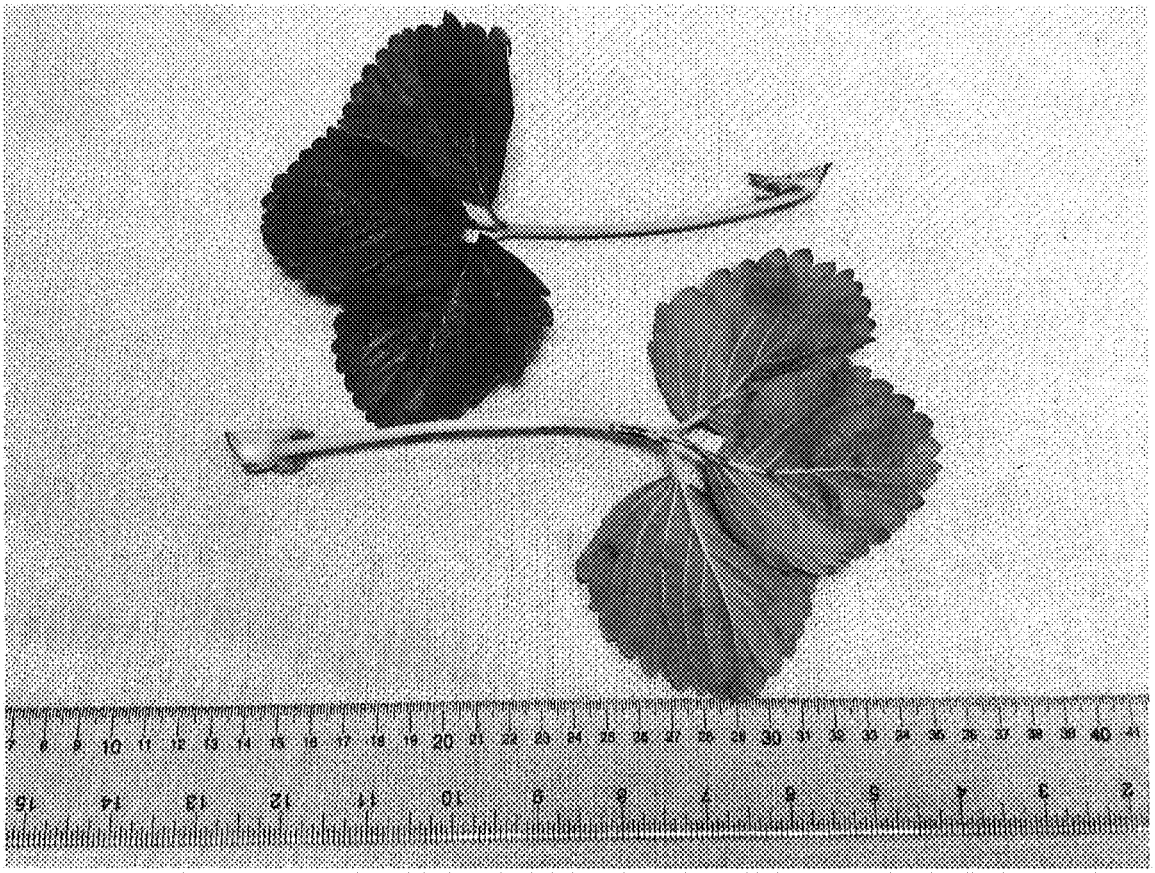
FIG. 4 shows upper and lower surfaces of leaf and leaf parts of 'BG-11.3209', taken in the month of April 2022.
Figure 5:
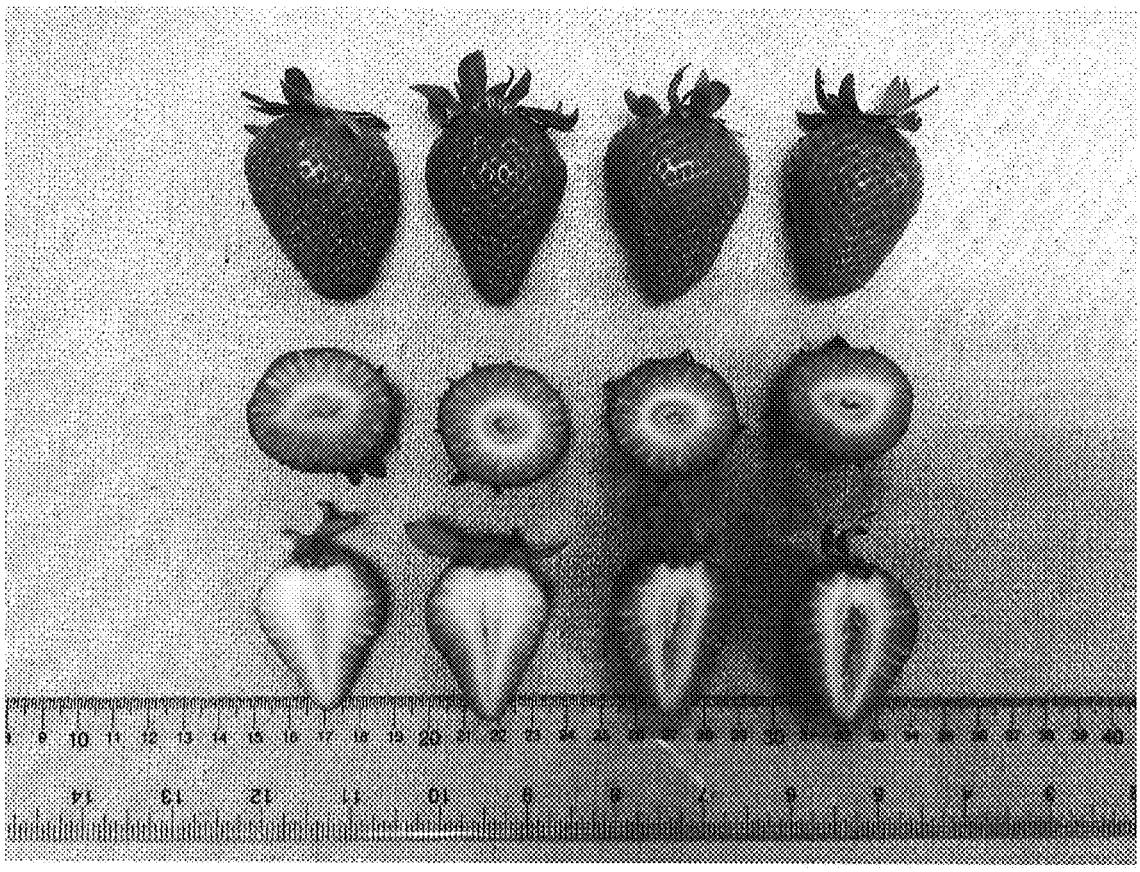
FIG. 5 shows internal and external mature fruit characteristics of 'BG-11.3209', taken in the month of April 2022.

The new variety 'BG-11.3209' has not been observed under all possible environmental conditions. The characteristics of the new variety 'BG-11.3209' may vary in detail, depending upon variations in environmental factors, including weather (temperature, humidity and light intensity), day length, soil type and location. In addition, the characteristics of any parental variety or comparison variety included in Tables 1, 2 and 3 of the present invention may vary in detail, depending upon variations in environmental factors, including weather (temperature, humidity and light intensity), day length, soil type and location.

The aforementioned photographs, together with the following description of the new variety 'BG-11.3209', unless otherwise noted, are based on observations taken during the 2022 growing season in Ventura County, Calif. These measurements and ratings were taken from plants of 'BG-11.3209' dug from a high-elevation nursery located in Siskiyou County, Calif. during early October 2021 and planted approximately four to five days later in Ventura County, Calif. The approximate age of the observed plants is five to six months. Yield observations including average weight and marketable yield, along with fruit quality characteristics including soluble solids, are averaged from seven years of data collected from the 2015 through 2021 growing seasons. Flower measurements and characteristics are from secondary flowers unless otherwise noted. Fruit characteristics and measurements are from secondary fruit, unless otherwise noted.

Where noted, color terminology follows The Royal Horticultural Society Colour Chart, London, Sixth Edition (2015).

The following characteristics describe fruit, plant, stolon, foliage, fruiting truss, flower, reproductive organs and pest and disease characteristics of the new strawberry 'BG-11.3209'.

Fruit characteristics:

*Color of mature fruit*.—RHS 45A (red).

*Color of internal flesh* (*excluding core*).—RHS 45C (medium red).

*Color of core*.—RHS 39B (medium red).

*Average length* (*cm*).—5.5.

*Average width* (*cm*).—4.4.

*Size*.—Large.

*Average length/width ratio*.—1.25 (much longer than broad).

*Hollow center average length* (*mm*).—2.4.

*Hollow center average width* (*mm*).—1.0.

*Hollow center expression*.—Moderate.

*Season average weight* (*gm*).—31.2.

*Marketable yield season* (*gm/plant*).—996.

*Predominant shape*.—Conical.

*Difference in shape between primary and secondary fruit*.—Ranges from slight to moderate.

*Band without achenes*.—Narrow.

*Evenness of surface*.—Slightly uneven.

*Evenness of color*.—Even or very slightly uneven.

*Glossiness*.—Ranges from medium to strong.
*Insertion of achenes*.—Ranges from level with surface to above surface.
*Average calyx diameter* (*cm*).—4.7.
*Position of calyx attachment*.—Ranges from level to raised.
*Attitude of sepals*.—Ranges from outward to upward.
*Size of calyx in relation to fruit diameter*.—Slightly larger.
*Adherence of calyx* (*when fully ripe*).—Strong.
*Firmness of flesh*.—Firm.
*Keeping quality*.—Ranges from good to moderate.
*Fruit market*.—Fresh.
*Post-harvest fruit longevity* (*at* 1 *to* 3 *degrees Celsius*).—5 to 7 days.
*Distribution of red color of the flesh*.—Marginal and central.
*Flavor*.—Very good.
*Soluble solids* (% *brix*).—8.7.
*Achene color, shaded side*.—RHS 153B (yellow green group).
*Achene color, sun-exposed side*.—RHS 185A (greyed purple group).
*Achene average length* (*mm*).—1.8.
*Achene average width* (*mm*).—0.8.
*Achene average weight* (*mg*).—0.58.
*Achene average quantity per berry*.—452.
*Achene shape*.—Elliptic.
*Flowering season* (50% *of plants with at least one flower*).—Medium (December in Ventura County, Calif.).
*Maturing season* (50% *of plants with mature fruit*).—Medium (January in Ventura County, Calif.).
*Flowering season*.—November to May (in Ventura County, Calif.).
*Harvest season*.—December to June (in Ventura County, Calif.).
*Harvest maturity*.—April (in Ventura County, Calif.).
*Plant hardiness*.—Zone 10 (USDA Plant Hardiness Zone Map).
*Type of bearing*.—Not remontant.

Plant characteristics:
*Average height* (*cm*).—17.8.
*Average spread* (*cm*).—28.7.
*Size*.—Medium.
*Habit*.—Upright.
*Density*.—Medium.
*Vigor*.—Medium.

Stolon characteristics:
*Color*.—RHS 146D (yellow green group).
*Anthocyanin coloration*.—RHS 182C (greyed red group).
*Anthocyanin intensity*.—Weak.
*Pubescence*.—Medium.
*Attitude of hairs*.—Upward.
*Average quantity in nursery* (*per square foot*).—5 to 8 (medium).
*Average diameter at the first bract* (*mm*).—3.2 (medium).
*Length from mother plant to first daughter* (*cm*).—28.4.

Terminal leaf characteristics:
*Average length* (*cm*).—6.6.
*Average width* (*cm*).—6.6.
*Average area terminal* ($cm^2$).—43.3.
*Average length/width ratio*.—1.0 (as long as broad).
*Shape of base*.—Obtuse.
*Shape of apex*.—Obtuse.
*Margins* (*shape of teeth*).—Obtuse (serrate to crenate).
*Average serrations per leaf*.—18.1.

Foliage characteristics:
*Color of upper surface*.—RHS 137B (medium yellow green).
*Color of lower surface*.—N148A (yellow green group).
*Color of venation, upper surface*.—RHS 137D (green group).
*Color of venation, lower surface*.—RHS 145C (yellow green group).
*Number of leaflets*.—3.
*Foliage size*.—Medium.
*Average length* (*cm*).—10.4.
*Average width* (*cm*).—14.4.
*Average area foliage* ($cm^2$).—150.4.
*Shape in cross section*.—Strongly to slightly concave.
*Interveinal blistering*.—Medium.
*Texture of upper surface*.—Medium.
*Texture of lower surface*.—Smooth.
*Venation pattern*.—Pinnate reticulate.
*Leaf glossiness*.—Strong.
*Leaf variegation*.—Absent.

Petiole characteristics:
*Petiole color*.—RHS 146D (yellow green group).
*Average length* (*cm*).—11.8.
*Average diameter* (*mm*).—3.6.
*Attitude of hairs*.—Slightly outward.
*Frequency of bract leaflets*.—40% occurrence (occasionally).
*Size of bract leaflets*.—Small.
*Pubescence*.—Moderate.
*Petiolule color*.—RHS 146D (yellow green group).
*Petiolule average length* (*mm*).—8.8.
*Petiolule average diameter* (*mm*).—1.9.

Stipule characteristics:
*Color*.—RHS 146C (yellow green group).
*Anthocyanin coloration*.—RHS 59C (red purple group).
*Anthocyanin intensity*.—Absent or very weak.
*Average length* (*mm*).—17.5.
*Average width* (*mm*).—10.3.
*Shape*.—Triangular.
*Texture*.—Light.
*Shape of base*.—N/A.
*Shape of apex*.—Acuminate.
*Margins*.—Entire (smooth).

Fruiting truss characteristics:
*Anthocyanin coloration*.—RHS 179B (greyed red group).
*Anthocyanin intensity*.—Ranges from medium to strong.
*Average length at maturity* (*cm*).—23.3.
*Position relative to foliage*.—Above.
*Flower quantity* (*season average per plant*).—35 to 45 (medium).
*Average fruit quantity per truss*.—5.6 (medium).
*Attitude at first pick*.—Prostrate.
*Primary pedicel color*.—RHS 146B (yellow green group).
*Primary pedicel average length* (*cm*).—22.2.
*Primary pedicel average diameter* (*mm*).—3.0.
*Pedicel attitude of hairs*.—Upward.
*Pedicel texture*.—Ranges from weak to medium.

*Primary peduncle color*.—RHS 146B (yellow green group).
*Primary peduncle average length* (*cm*).—1.1.
*Primary peduncle average diameter* (*mm*).—8.4.
*Peduncle texture*.—Ranges from weak to medium.

Flower characteristics:
*Petal color, upper surface*.—RHS NN155C (white group).
*Petal color, lower surface*.—RHS NN155C (white group).
*Petal average length* (*mm*).—11.3.
*Petal average width* (*mm*).—11.7.
*Petal average length/width ratio*.—0.96 (as long as broad).
*Average petal quantity per flower*.—5.5.
*Petal shape*.—Obovate.
*Petal texture, upper surface*.—Smooth.
*Petal texture, lower surface*.—Smooth.
*Petal shape of base*.—Obtuse.
*Petal shape of apex*.—Rounded.
*Petal margins*.—Entire (smooth).
*Sepal color, upper surface*.—RHS 138A (green group).
*Sepal color, lower surface*.—RHS 138B (green group).
*Sepal average length* (*mm*).—15.3.
*Sepal average width* (*mm*).—7.0.
*Sepal average length/width ratio*.—2.18.
*Average sepal quantity per flower*.—11.0.
*Sepal shape*.—Ovate.
*Sepal texture, upper surface*.—Light.
*Sepal texture, lower surface*.—Light.
*Sepal shape of apex*.—Acute.
*Sepal margins*.—Entire (smooth).
*Corolla average diameter* (*mm*).—27.8 (medium).
*Flower average depth* (*mm*).—11.5 (medium).
*Calyx average diameter* (*mm*).—39.3.
*Size of calyx relative to corolla*.—Larger.
*Relative position of petals* (*flowers with* 5 *or* 6 *petals*).—Overlapping.
*Size of inner calyx relative to outer calyx*.—Smaller.

Reproductive organs:
*Anther color*.—RHS 12A (yellow group).
*Filament color*.—RHS 145C (yellow green group).
*Filament average length* (*mm*).—2.1.
*Anther average length* (*mm*).—1.2.
*Anther average width* (*mm*).—0.9.
*Anther shape*.—Elliptic.
*Pollen amount*.—Abundant.
*Ovary color*.—RHS 147B (yellow green group).
*Style color*.—RHS 151D (yellow green group).
*Pistil average quantity per flower*.—452.
*Pistil average length* (*mm*).—1.1.
*Style average length* (*mm*).—1.0.
*Stigma average diameter* (*mm*).—0.3.
*Stigma shape*.—Rounded.

Disease and pest reactions:
*Powdery mildew* (*sphaerotheca macularis*).—Moderately susceptible.
*Botrytis fruit rot* (*botrytis cinerea*).—Moderately susceptible.
*Fusarium wilt* (*fusarium oxysporum*).—Moderately susceptible.
*Two-spotted spider mite* (*tetranychus urticae*).—Moderately susceptible.

We claim:

1. A new and distinct strawberry plant named 'BG-11.3209', as herein described and illustrated by the characteristics set forth above.

* * * * *